(12) United States Patent
Palmer et al.

(10) Patent No.: US 7,322,935 B2
(45) Date of Patent: Jan. 29, 2008

(54) ENDOSCOPIC RETRACTOR

(75) Inventors: Matthew A. Palmer, Miami, FL (US); Jose Luis Francese, Miami Springs, FL (US); Ralph de la Torre, Swampscott, MA (US)

(73) Assignee: Medcanica, LLC, Miami, FL (US)

( * ) Notice: Subject to any disclaimer, the term of this patent is extended or adjusted under 35 U.S.C. 154(b) by 303 days.

(21) Appl. No.: 10/348,845

(22) Filed: Jan. 22, 2003

(65) Prior Publication Data

US 2004/0143163 A1 Jul. 22, 2004

(51) Int. Cl.
*A61B 1/32* (2006.01)
(52) U.S. Cl. .................................... 600/204
(58) Field of Classification Search ............. 600/204, 600/208, 210, 215, 216, 219, 222, 225
See application file for complete search history.

(56) References Cited

U.S. PATENT DOCUMENTS

| | | | | | |
|---|---|---|---|---|---|
| 4,877,030 | A | * | 10/1989 | Beck et al. .................. | 606/195 |
| 5,178,133 | A | * | 1/1993 | Pena .......................... | 600/203 |
| 5,190,561 | A | * | 3/1993 | Graber ........................ | 606/127 |
| 5,195,505 | A | * | 3/1993 | Josefsen ..................... | 600/204 |
| 5,235,966 | A | * | 8/1993 | Jamner ........................ | 600/204 |
| 5,304,187 | A | * | 4/1994 | Green et al. ................. | 606/151 |
| 5,320,627 | A | * | 6/1994 | Sorensen et al. ............ | 606/128 |
| 5,353,784 | A | * | 10/1994 | Nady-Mohamed .......... | 600/205 |
| 5,370,650 | A | * | 12/1994 | Tovey et al. ................. | 606/151 |
| 5,490,819 | A | * | 2/1996 | Nicholas et al. ............ | 600/201 |
| 5,514,157 | A | * | 5/1996 | Nicholas et al. ............ | 606/206 |
| 5,547,458 | A | * | 8/1996 | Ortiz et al. .................. | 600/204 |
| 5,556,376 | A | * | 9/1996 | Yoon .......................... | 604/15 |
| 5,620,458 | A | * | 4/1997 | Green et al. ................. | 606/188 |
| 5,662,676 | A | * | 9/1997 | Koninckx ................... | 606/198 |
| 5,700,275 | A | * | 12/1997 | Bell et al. ................... | 606/208 |
| 5,755,661 | A | * | 5/1998 | Schwartzman ............. | 600/216 |
| 5,803,902 | A | * | 9/1998 | Sienkiewicz et al. ....... | 600/203 |
| 6,156,045 | A | * | 12/2000 | Ulbrich et al. .............. | 606/151 |
| 6,221,008 | B1 | * | 4/2001 | Keckstein et al. .......... | 600/204 |
| 6,248,062 | B1 | * | 6/2001 | Adler et al. ................. | 600/204 |
| 6,354,995 | B1 | * | 3/2002 | Hoftman et al. ............ | 600/219 |
| 6,416,506 | B1 | * | 7/2002 | Tilton et al. ................. | 606/1 |
| 6,605,105 | B1 | * | 8/2003 | Cuschieri et al. ........... | 606/208 |
| 6,817,972 | B2 | * | 11/2004 | Snow .......................... | 600/37 |
| 2002/0111536 | A1 | * | 8/2002 | Cuschieri et al. ........... | 600/210 |

(Continued)

*Primary Examiner*—Eduardo C. Robert
*Assistant Examiner*—Michael B Priddy
(74) *Attorney, Agent, or Firm*—Gordon & Jacobson, PC

(57) ABSTRACT

An endoscopic retractor includes a tube having a proximal end and a distal end with a push rod extending therethrough. The proximal ends of the push rod is provided with a threaded portion. A rotatable handle is coupled to the proximal end of the tube and threadably engages the threaded portion of the push rod such that rotation of the handle causes a translation of the push rod. The distal end of the tube is provided with a clevis through which the distal end of the push rod extends. A multi-segment canopy is coupled to the clevis and the push rod via an articulate linkage. Translation of the push rod in the distal direction causes the canopy to be moved from a starting substantially cylindrical configuration with its axis nearly collinear with the axis of the tube to an opened quasi-planar configuration. Further translation of the push rod in the distal direction causes the quasi-planar canopy to be rotated in the clevis to an angle of approximately ninety degrees relative to the axis of the tube.

52 Claims, 9 Drawing Sheets

U.S. PATENT DOCUMENTS

2003/0055318 A1* 3/2003 Vierra et al. ................ 600/204
2004/0082837 A1* 4/2004 Willis ......................... 600/210
2004/0254425 A1* 12/2004 Vierra et al. ................ 600/204

* cited by examiner

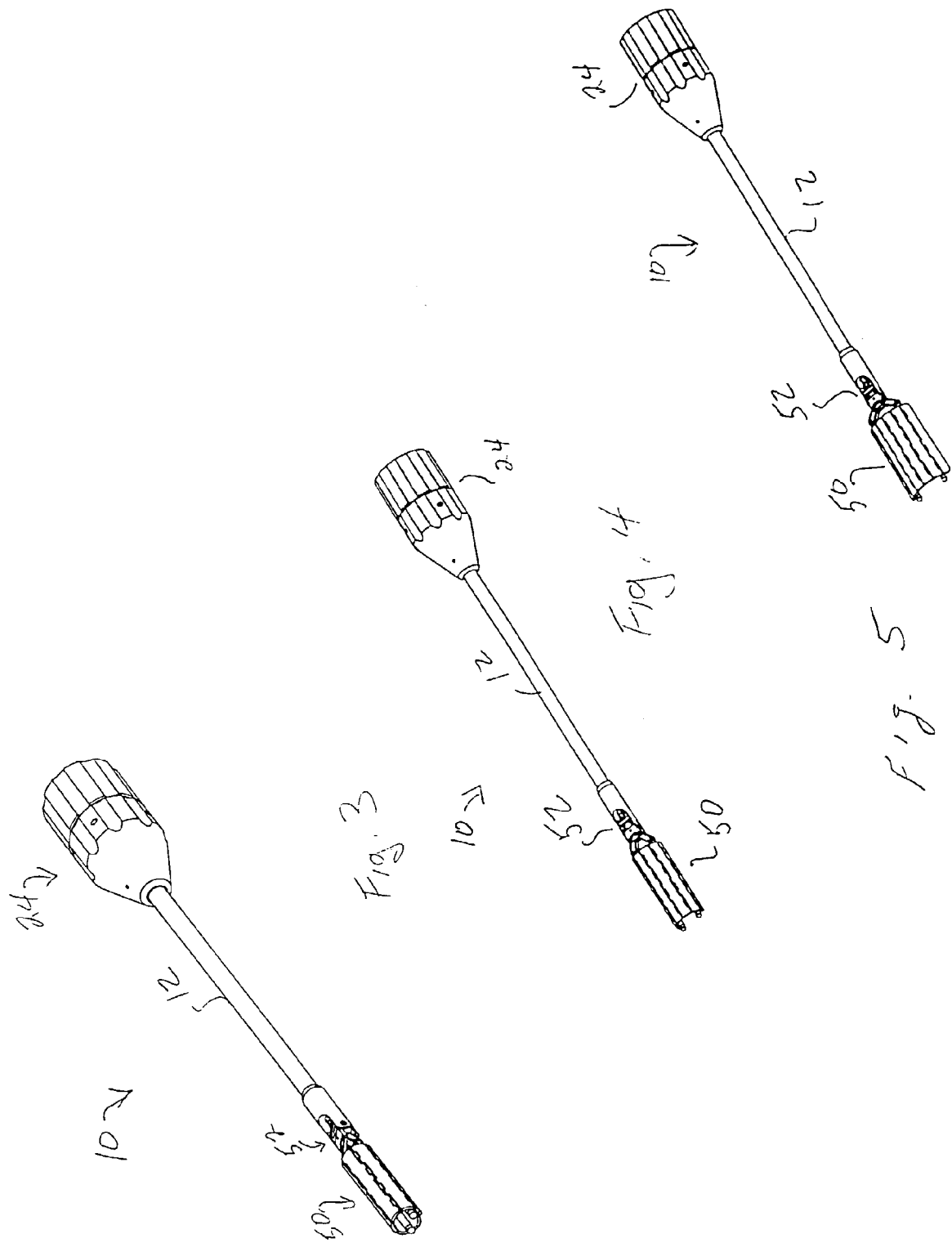

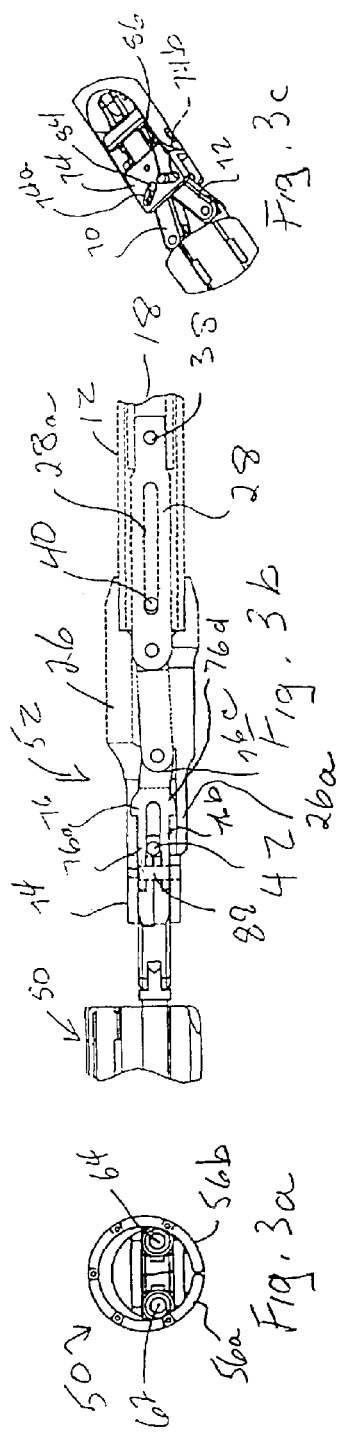

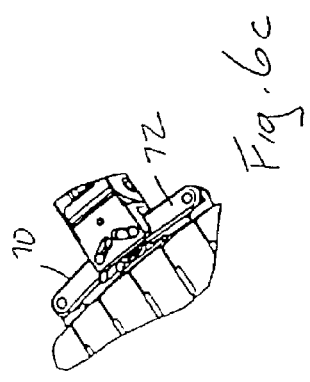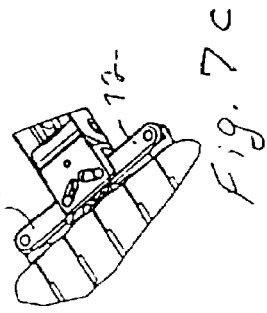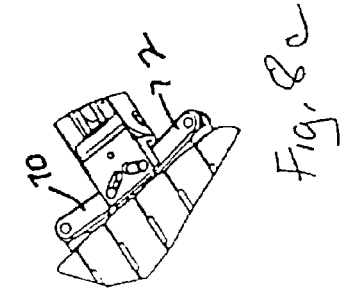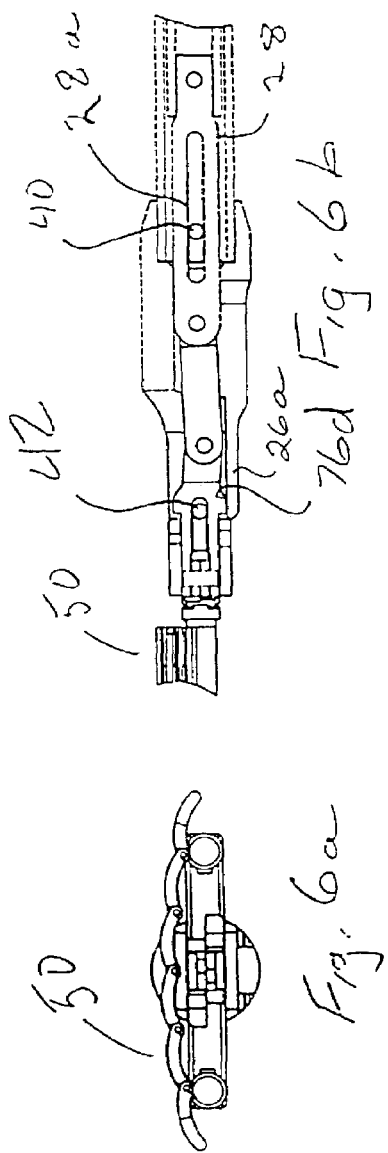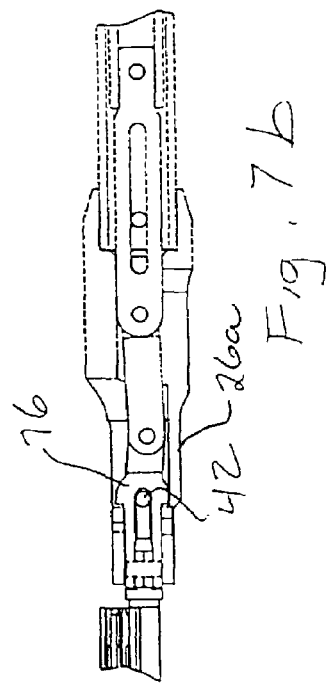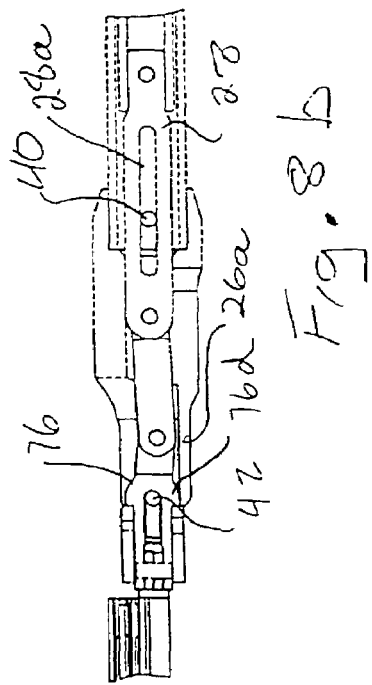

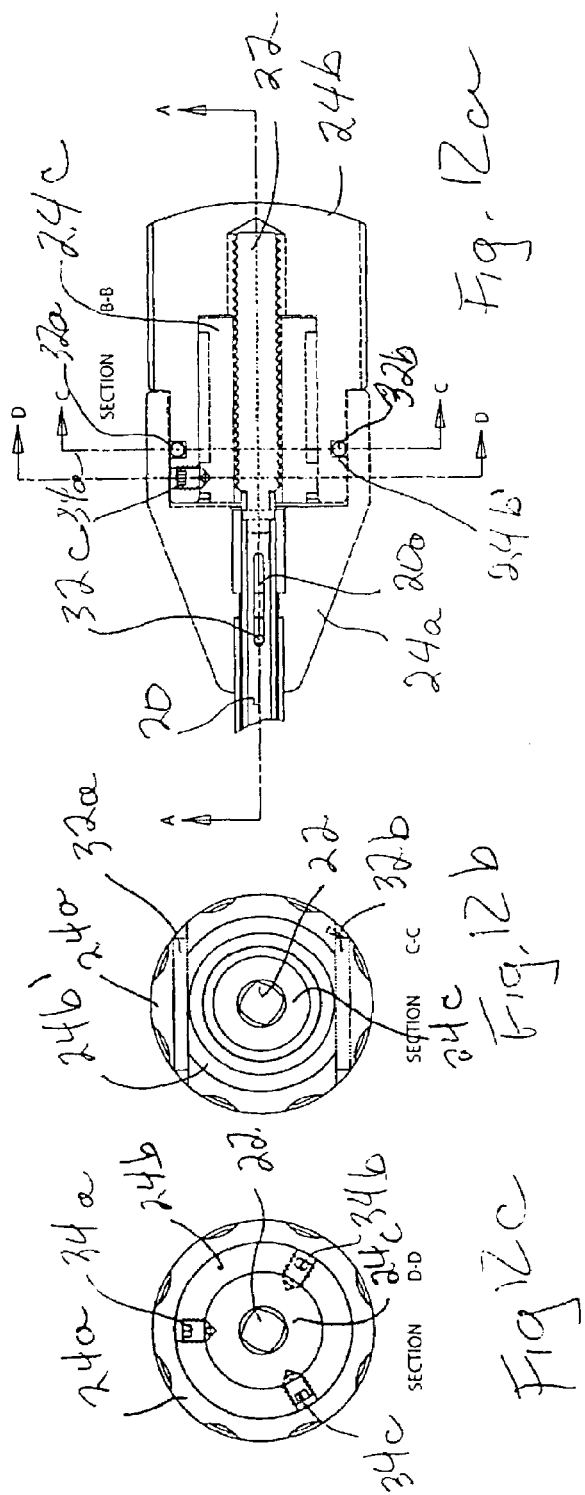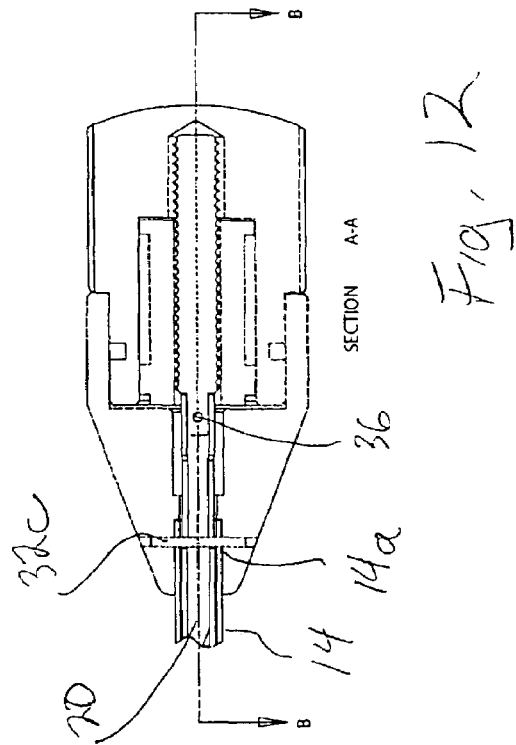

ENDOSCOPIC RETRACTOR

BACKGROUND OF THE INVENTION

1. Field of the Invention

The invention relates to apparatus for performing minimally invasive surgery. More particularly, the invention relates to a retractor instrument suitable for use in endoscopic/laparoscopic surgery.

2. State of the Art

In many surgical procedures it is necessary to retract or pull up on internal tissue structures to create space and to gain access to the operative site. In minimally invasive surgeries this is a particularly challenging task because of the limitations posed by the small incision. Small incisions are made with trocars inside trocar tubes which puncture the body wall. The trocars are removed from the tubes and the tubes are left in place to provide ports to the interior of the body. The diameter of trocar tubes is in the range of 5-20 mm. Generally, the structures that need to be retracted within the body are large and require considerable force to move and keep away from the workspace. Such structures are not likely to fit through the narrow opening provided by a trocar tube.

U.S. Pat. No. 5,514,157 issued May 7, 1996 to Nicholas et al. discloses a plurality of articulating endoscopic surgical tools including a retractor. The retractor consists of three layered blades which can be opened like a fan and then angled relative to the shaft of the instrument. The apparatus utilizes two separate rods to operate the retractor. One rod is pulled back to spread the blades and the other rod is pushed forward to angle the blades relative to the axis of the instrument. The first rod must be flexible to bend as much as the retractor is angled. Thus, the first rod may be subject to breaking or kinking. The second rod is movable from one cam locked position to a second cam locked position. Thus, the angling of the retractor is limited to two positions, zero and forty-five degrees. The three blades can be spread to span a distance approximately three times the diameter of the shaft of the apparatus. However, when spread, the blades form spaces between each other. In other words, the spread blades do not form a unitary surface but three small surfaces with spaces between them.

SUMMARY OF THE INVENTION

It is therefore an object of the invention to provide a retractor apparatus which can enter the surgical site through a small incision.

It is also an object of the invention to provide a retractor apparatus which is capable of strong rigid retraction.

It is another object of the invention to provide a retractor apparatus which is continuously adjustable to any angle between zero and ninety degrees.

It is still another object of the invention to provide an endoscopic retractor apparatus which is suitable for use in heart surgery.

In accord with these objects which will be discussed in detail below, the apparatus of the present invention preferably includes a tube having a proximal end and a distal end with a push rod extending therethrough. The proximal end of the push rod is provided with a threaded portion. A rotatable handle is coupled to the proximal end of the tube and threadably engages the threaded portion of the push rod such that rotation of the handle causes a translation of the push rod. The distal end of the tube is provided with a clevis through which the distal end of the push rod extends. A multi-segment canopy is coupled to the clevis and the push rod via an articulate linkage. Translation of the push rod in the distal direction causes the canopy to be moved from a starting substantially cylindrical configuration with its axis nearly collinear with the axis of the tube to an opened quasi-planar configuration. Further translation of the push rod in the distal direction causes the quasi-planar canopy to be rotated in the clevis to an angle of approximately ninety degrees relative to the axis of the tube.

When in the quasi-planar configuration, the canopy has a width approximately three times the diameter of the instrument. However the length of the canopy may be substantial. The quasi-planar configuration is a substantially continuous rectangle with no large spaces. The rigid articulating linkage between the canopy and the push rod provides for a strong rigid retraction capability.

Retraction is achieved by deploying the canopy under tissue and pulling on the tube to lift the tissue. To maintain tissue in the retracted position the tube can be held by a clamp or an anchoring port.

Additional objects and advantages of the invention will become apparent to those skilled in the art upon reference to the detailed description taken in conjunction with the provided figures.

BRIEF DESCRIPTION OF THE DRAWINGS

FIG. 3 is an assembled perspective view of the endoscopic retractor with the canopy in a first closed position;

FIG. 3a is a transverse sectional view of the canopy in the first closed position;

FIG. 3b is a broken longitudinal section illustrating the canopy, clevis, push rod, and articulate linkage in the first closed position;

FIG. 3c is a broken perspective view of the canopy, clevis, and linkage in the first closed position;

FIG. 4 is an assembled perspective view of the endoscopic retractor with the canopy in a second partially open position;

FIG. 4a is a front view of the canopy in the second partially open position;

FIG. 4b is a broken longitudinal section illustrating the canopy, clevis, push rod, and articulate linkage in the second partially open position;

FIG. 4c is a broken perspective view of the canopy, clevis, and linkage in the second partially open position;

FIG. 5 is an assembled perspective view of the endoscopic retractor with the canopy in a third partially open position;

FIG. 5a is a front view of the canopy in the third partially open position;

FIG. 5b is a broken longitudinal section illustrating the canopy, clevis, push rod, and articulate linkage in the third partially open position;

FIG. 5c is a broken perspective view of the canopy, clevis, and linkage in the third partially open position;

FIG. 6a is a front view of the canopy in the fourth partially open position;

FIG. 6b is a broken longitudinal section illustrating the canopy, clevis, push rod, and articulate linkage in the fourth partially open position;

FIG. 6c is a broken perspective view of the canopy, clevis, and linkage in the fourth partially open position;

FIG. 7a is a front view of the canopy in the fifth fully open position;

FIG. 7b is a broken longitudinal section illustrating the canopy, clevis, push rod, and articulate linkage in the fifth fully open position;

FIG. 7c is a broken perspective view of the canopy, clevis, and linkage in the fifth fully open position;

FIG. 8a is a front view of the canopy in the sixth over the center open position;

FIG. 8b is a broken longitudinal section illustrating the canopy, clevis, push rod, and articulate linkage in the sixth over the center open position;

FIG. 8c is a broken perspective view of the canopy, clevis, and linkage in the sixth over the center open position;

FIGS. 12, 12a-12c are sectional views of the presently preferred handle assembly.

DETAILED DESCRIPTION OF THE PREFERRED EMBODIMENTS

Figure 1:
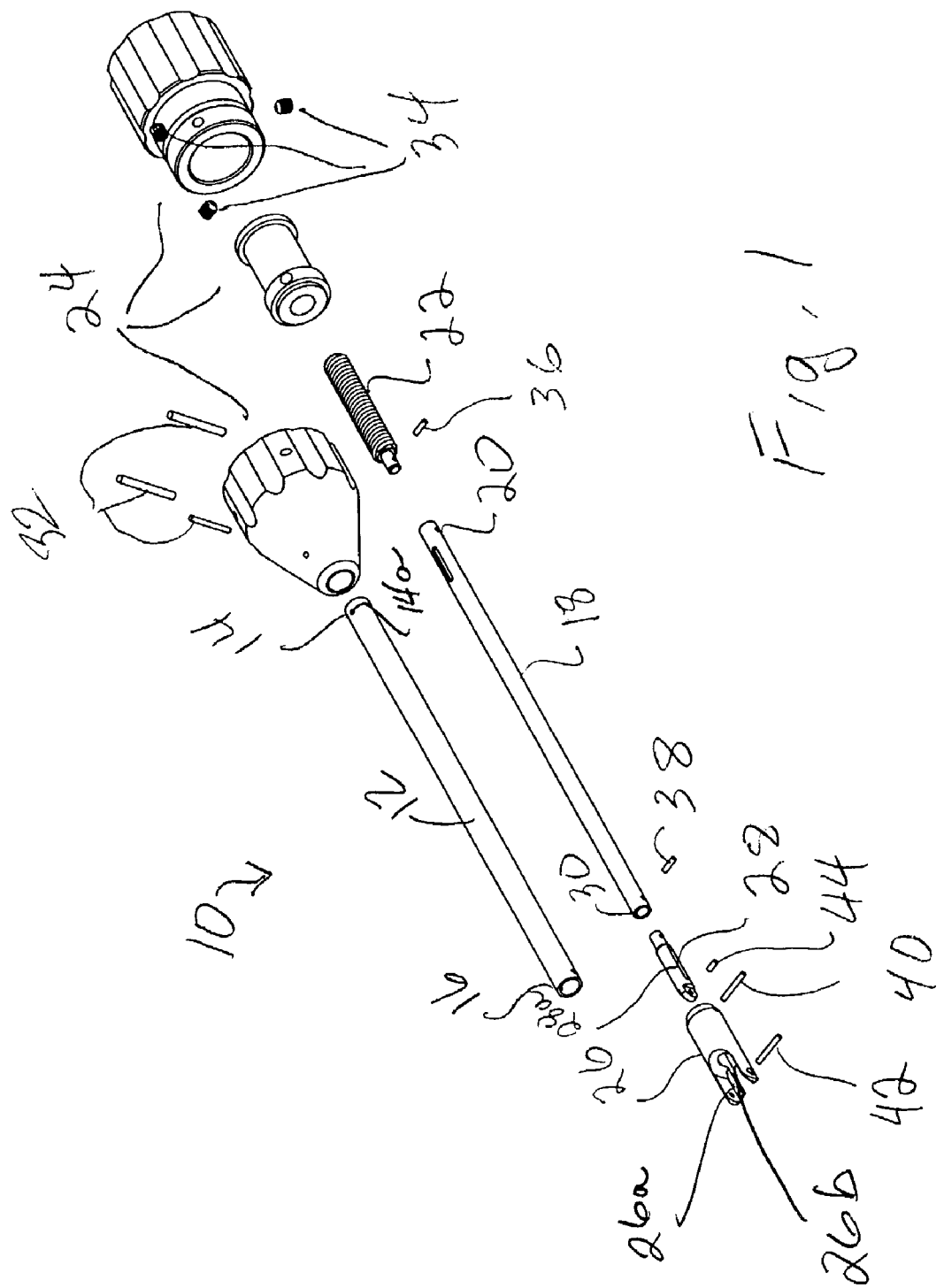
FIG. 1 is an exploded perspective view of the tube, push rod, handle, and clevis of the invention.
Figure 2:
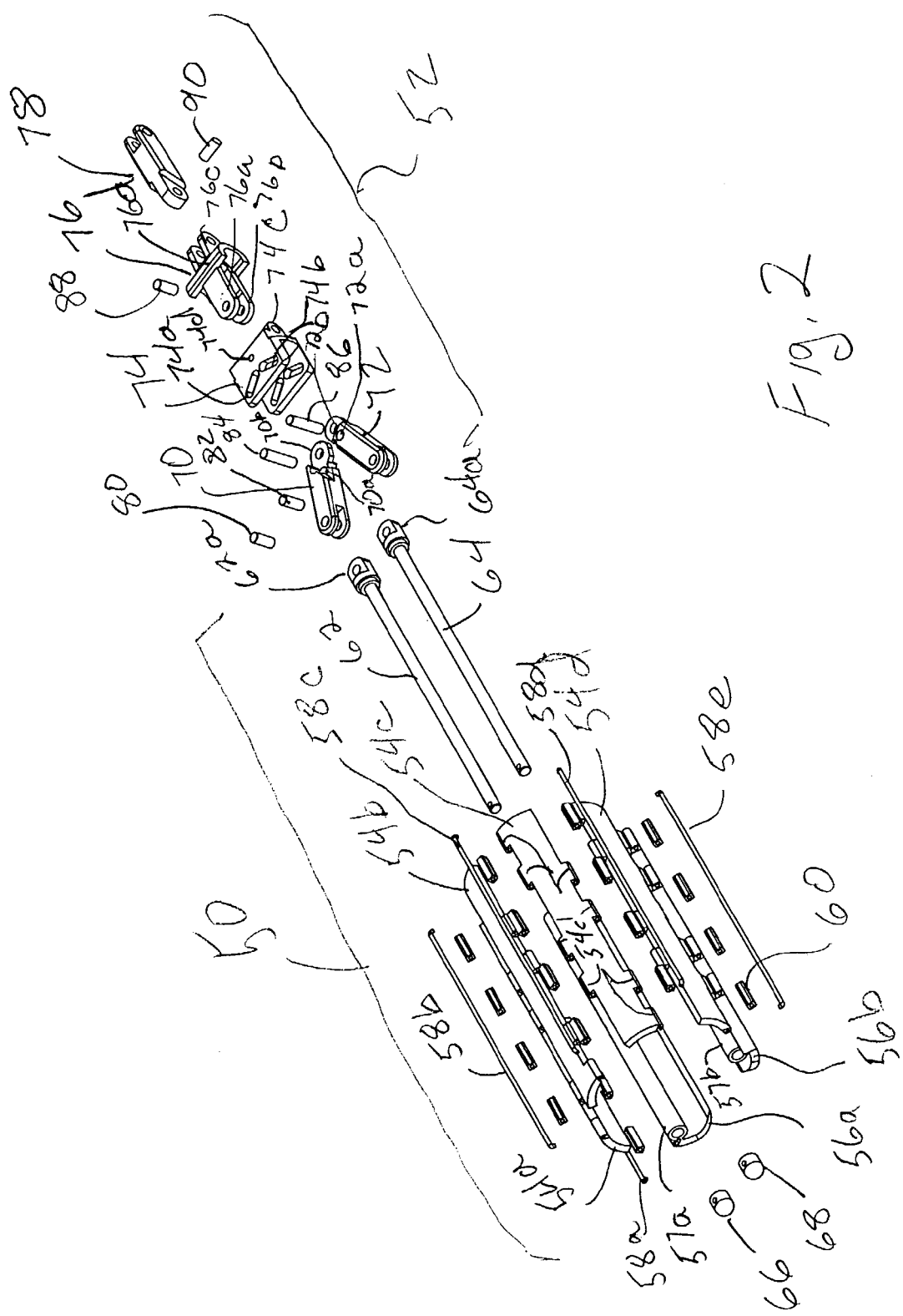
FIG. 2 is an exploded perspective view of the canopy and the articulate linkage of the invention.
Figure 6:
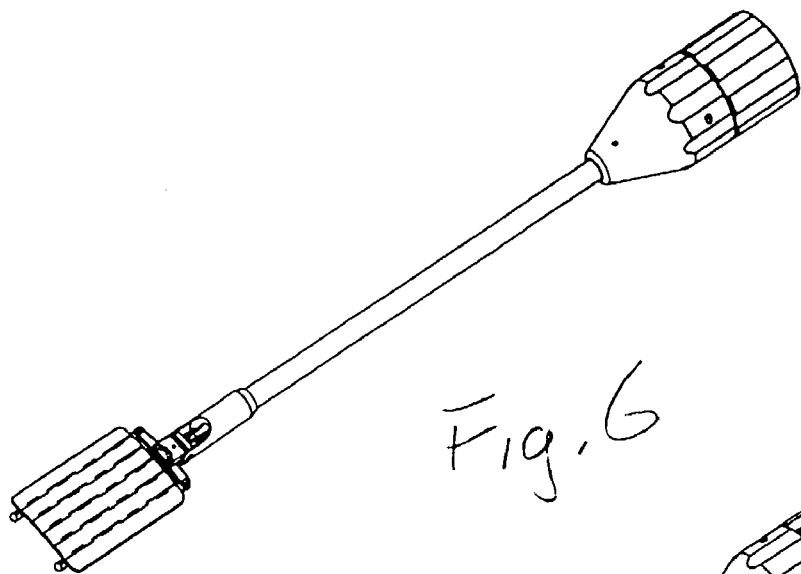
FIG. 6 is an assembled perspective view of the endoscopic retractor with the canopy in a fourth partially open position.
Figure 7:
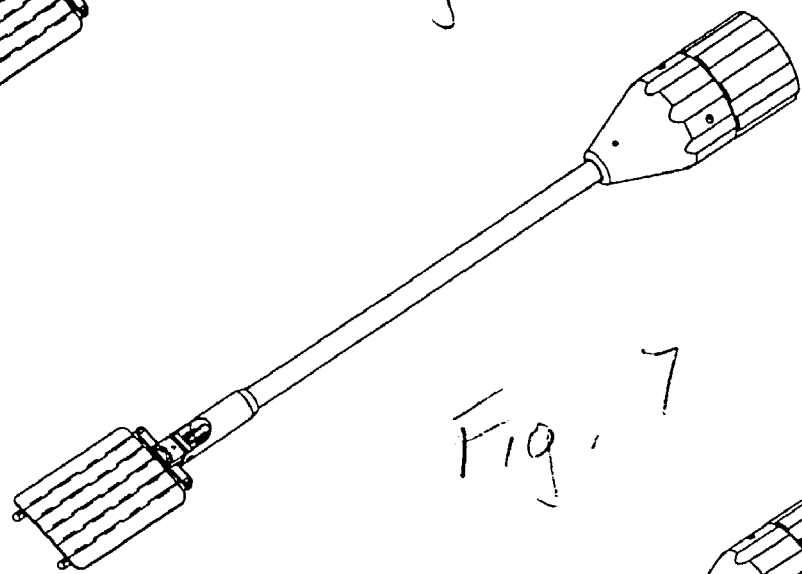
FIG. 7 is an assembled perspective view of the endoscopic retractor with the canopy in a fifth fully open position.

Referring now to FIGS. 1 through 3, the apparatus 10 of the present invention includes a tube 12 having a proximal end 14 and a distal end 16 with a push rod 18 extending therethrough. The proximal end 20 of the push rod 18 is provided with a threaded portion 22. A rotatable handle assembly 24 is coupled to the proximal end 14 of the tube 12 and threadably engages the threaded portion 22 of the push rod 18 such that rotation of the handle causes a translation of the push rod. The handle assembly 24 is described in more detail below with reference to FIGS. 12, 12a, 12b, and 12c.

The distal end 16 of the tube 12 is provided with a clevis 26 through which a driving link 28 coupled to the distal end 30 of the push rod 18 extends. As shown in FIG. 1, the handle assembly 24 includes three pieces which are attached to each other by pins 32 and set screws 34. The threaded portion 22 of the push rod 18 is coupled to the proximal end 20 by pin 36. The driving link 28 is coupled to the distal end 30 of the push rod 18 by a pin 38. The clevis 26 is coupled to the distal end 16 of the tube 12 by pin 40 and is provided with a clevis axle 42. As seen better in FIGS. 3b, 4b, etc., the driving link 28 is provided with a longitudinal slot 28a through which the clevis mounting pin 40 passes. Thus, the clevis mounting pin 40 serves to limit movement of the driving link 28 as well as secure the clevis to the tube 12. FIG. 1 also shows that the clevis 26 has two lower interior shoulders 26a, 26b which aid in guiding the linkage as described in more detail below with reference to FIGS. 3b through 8b.

FIG. 2 illustrates a multi-segment canopy 50 and an articulate linkage 52 which are coupled to the clevis 26 and the driving link 28 of FIG. 1.

The multi-segment canopy 50 includes four substantially identical canopy mid-segments 54a, 54b, 54c, 54d, two substantially identical canopy end segments 56a, 56b, five hinge axles 58a, 58b, 58c, 58d, 58e, and sixteen hinge stops 60 (only one of which is labeled to avoid congestion). It will be appreciated that the segments need not be identical so long as they are similar enough to fit together. As shown in the Figures, the canopy segments are arcuate. The segments of the canopy have spaced apart hinge gudgens (e.g. 54c') which interengage each other and are held together with the axles (pintles). The hinge stops are located on the axles interleaved between the gudgeons. The hinge stops are cylindrical with at least one radial projection. They prevent the canopy segments from hinging beyond the maximal deployed position but do not hinder closing of the canopy. According to the presently preferred embodiment, the axles 58a, 58b, 58c, 58d, 58e are torsion springs which are coupled to the canopy segments in such a way as to bias the canopy 50 to the closed position shown in FIG. 3a. The end segments 56a, 56b are provided with long interior gudgeons 57a, 57b which are engaged by canopy arms 62, 64. The canopy arms are maintained in place by retention caps 66, 68. The proximal end of each arm is provided with a link coupling 62a, 64a.

The articulate linkage 52 includes a pair of canopy actuation links 70, 72, a gimbal 74, a camming link 76, and an angling link 78. The distal ends of the links 70, 72 are coupled to the proximal couplings 62a, 64a of the canopy arms with pins 80, 82. The proximal ends of the links 70, 72 each have two holes 70a, 72a and 70b, 72b. The holes 70a, 72a are designed to receive pins 84, 86 which reside in angled slots 74a, 74b of the gimbal 74. The holes 70b, 72b are designed to overlie each other and receive pin 88 which couples the links to the camming link 76. More particularly, the proximal end of the gimbal 74 is provided with a transverse bore 74c which is coupled to the clevis 26 by the clevis axle 42. The camming link 76 has a pair of distal arms 76a, 76b which extend through bores (not shown) the proximal end of the gimbal 74 on opposite sides of the transverse bore 74c. These arms are joined by the pin 88 which is inserted through a bore 74d in the gimbal 74 but which does not interfere with the movement of the arms into and out of the proximal end of the gimbal 74. As mentioned above, the pin 88 couples the camming link 76 to the canopy actuation links 70, 72 by extending through the holes 70b, 72b in the links. The camming link 76 is provided with a slightly downwardly disposed proximal link 76c (seen best in FIGS. 3b, 4b, etc.) which is coupled to the angle link 78 by pin 90. Between the two arms 76a, 76b and the downward proximal link 76c, the camming link 76 has a radiused surface 76d. The proximal end of the angle link 78 is coupled to the driving link 26 by the pin 44 shown in FIG. 1.

FIG. 3 illustrates the apparatus 10 fully assembled with the handle assembly 24 rotated to a first position such that the multi-element canopy 50 assumes a substantially cylindrical configuration with its axis approximately collinear with the axis of the tube 12. In this first position, the canopy 50 has a diameter suitable for passing through a trocar tube or the like. According to the presently preferred embodiment, the canopy has a diameter of approximately 15 mm when in this configuration. As mentioned above, the axles coupling the canopy segments are preferably torsion springs which bias the canopy to the position shown in FIG. 3.

FIGS. 3a-3c also show the apparatus in this first position. FIG. 3a illustrates a transverse section of the canopy. FIG. 3b illustrates a broken longitudinal section of the canopy 50, the articulate linkage 52, and the clevis 26. FIG. 3c illustrates a broken perspective view of the canopy 50, the articulate linkage 52, and the clevis 26.

As seen best in FIG. 3a, when in this first position, the canopy end segments 56a, 56b and the canopy arms 62, 64 are in their closest (adjacent) positions.

As seen best in FIG. 3b, when the apparatus 10 is in this first position, the distal end of the slot 28a in the driving link is close to or abuts the pin 40 which couples the clevis 26 to the distal end of the tube 12. It will be appreciated that the push rod 18 is thus in or near the proximal-most position. Accordingly, the arms 76a, 76b of the camming link 76 are nearly withdrawn from the gimbal 74 with the pin 88 close to or abutting the clevis axle 42. In addition, the radiused surface 76d of the camming link is in sliding contact with the clevis shoulders 26a, (26b not shown). This prevents the camming link from rotating about the clevis axle 42.

As seen best in FIG. 3c, in this first position, the pins 84, 86 of the actuation links 70, 72 are in the proximal innermost parts of the slots 74a, 74b.

Turning now to FIGS. 4, 4a, 4b, and 4c, following rotation of the handle 24, the push rod 18 is advanced distally. This moves the driving link 28 and the angling link 78 distally which pushes the camming link 76 further into the gimbal 74.

As seen best in FIG. 4c, distal advancement of the camming link 76 moves the canopy actuation links 70, 72 as guided by the pins 84, 84 in the slots 74a, 74b. This increases the angle between the links 70, 72 which causes a separation of the canopy arms 62, 64. As seen best in FIG. 4a, movement of the canopy arms apart from each other causes the end segments 56a, 56b of the canopy to be moved apart.

FIGS. 5, 5a, 5b, and 5c illustrate the apparatus after further rotation of the handle. As seen best in FIG. 5d, the canopy 50 no longer resembles a cylinder but only a segment of a cylinder.

FIGS. 6, 6a, 6b, and 6c illustrate the apparatus after still further rotation of the handle. As seen best in FIG. 6a, the canopy 50 is approaching a near planar configuration. As seen best in FIG. 6b, the camming link 76 is approaching its maximum distal position as determined by the clevis axle 42. At this location, the radiused surface 76d of the camming link is approaching the distal ends of the clevis shoulders 26a, (26b not shown). It should be noted that the driving link 28 is not even half way to its maximum distal position as determined by pin 40 in slot 28a. As seen best in FIG. 6c, the angle between the links 70, 72 is approaching 180°.

FIGS. 7, 7a, 7b, and 7c illustrate the apparatus after still further rotation of the handle. As seen best in FIG. 7c, the angle between the links 70, 72 is now 180°. However, as seen best in FIG. 7b, further movement of the camming link 76 is not yet prevented by the clevis axle 42.

Figure 8:
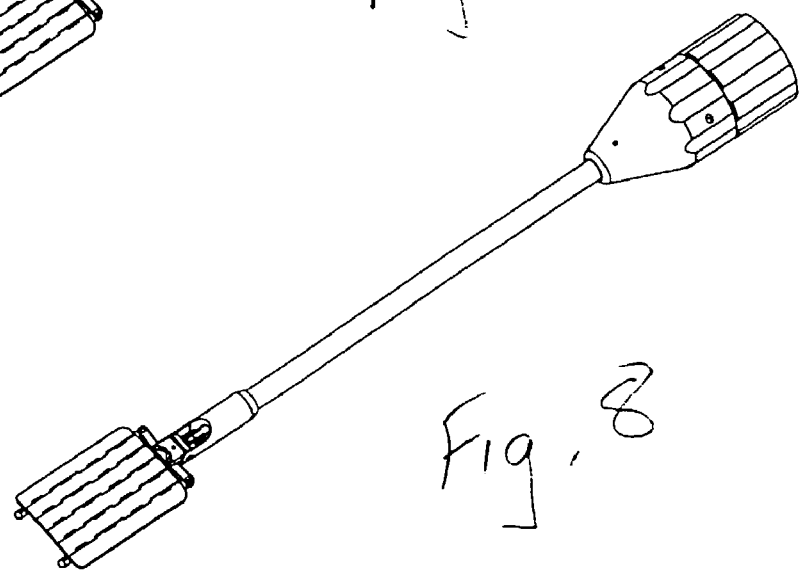
FIG. 8 is an assembled perspective view of the endoscopic retractor with the canopy in a sixth over the center open position.
Figure 9:
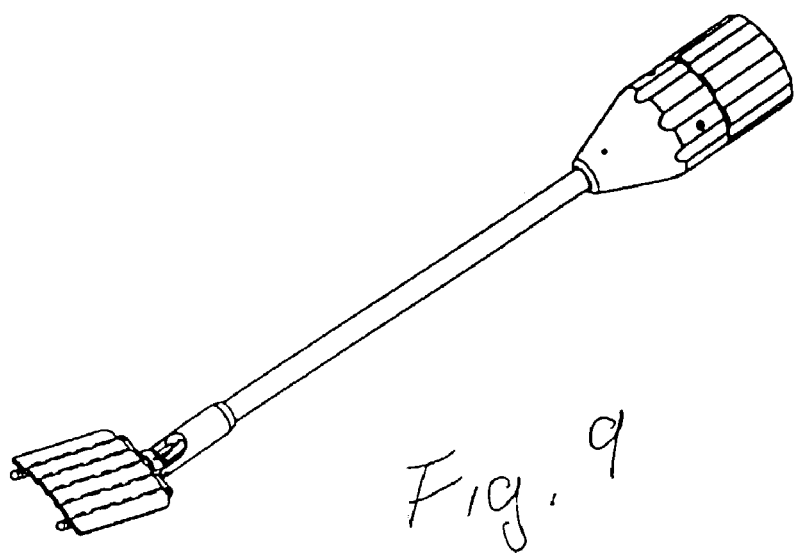
FIG. 9 is an assembled perspective view of the endoscopic retractor with the canopy in a first stage of angulation.
Figure 10:
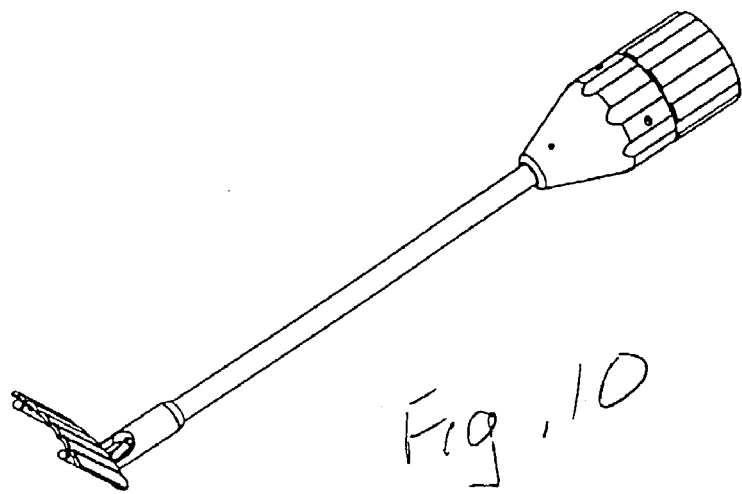
FIG. 10 is an assembled perspective view of the endoscopic retractor with the canopy in a second stage of angulation.
Figure 11:
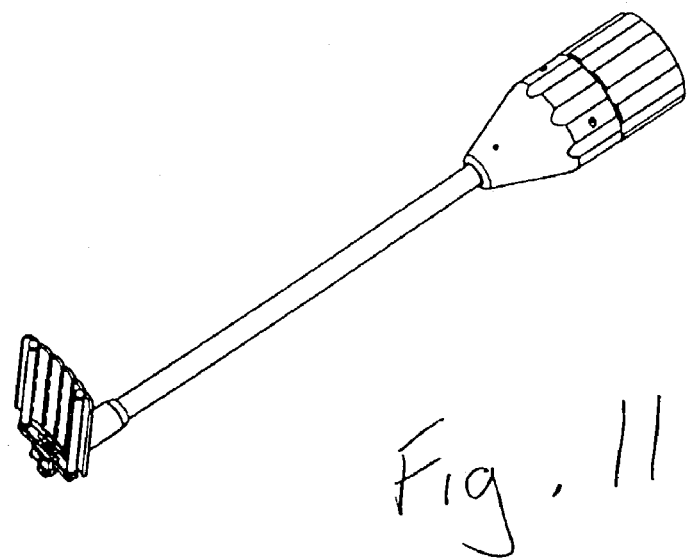
FIG. 11 is an assembled perspective view of the endoscopic retractor with the canopy in a third stage of angulation.
Figure 9C:
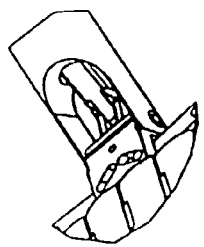
FIG. 9c is a broken perspective view of the canopy, clevis, and linkage in the first stage of angulation.
Figure 10C:
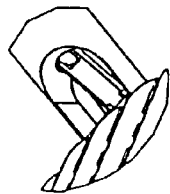
FIG. 10c is a broken perspective view of the canopy, clevis, and linkage in the second stage of angulation.
Figure 11C:
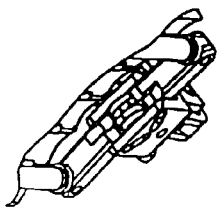
FIG. 11c is a broken perspective view of the canopy, clevis, and linkage in the third stage of angulation.
Figure 9B:
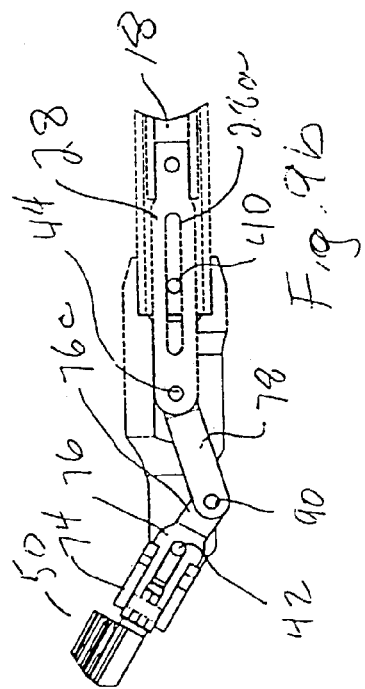
FIG. 9b is a broken longitudinal section illustrating the canopy, clevis, push rod, and articulate linkage in the first stage of angulation.
Figure 10B:
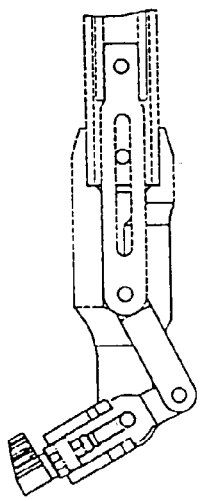
FIG. 10b is a broken longitudinal section illustrating the canopy, clevis, push rod, and articulate linkage in the second stage of angulation.
Figure 11B:
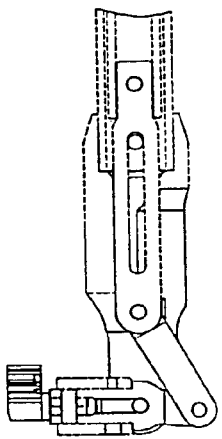
FIG. 11b is a broken longitudinal section illustrating the canopy, clevis, push rod, and articulate linkage in the third stage of angulation.
Figure 9A:
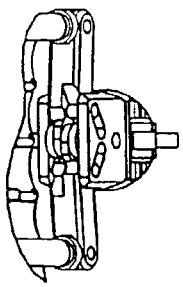
FIG. 9a is a front view of the canopy in the first stage of angulation.
Figure 10A:
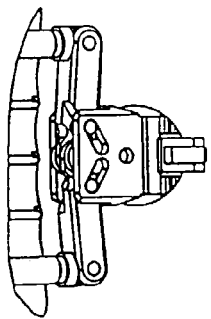
FIG. 10a is a front view of the canopy in the second stage of angulation.
Figure 11A:
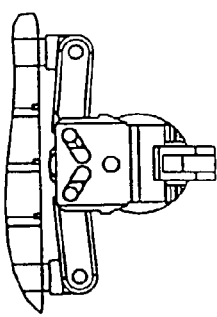
FIG. 11a is a front view of the canopy in the third stage of angulation.

Referring now to FIGS. 8, 8a, 8b, and 8c, further distal movement of the camming link 76 is ultimately prevented by the clevis axle 42. When the camming link abuts the clevis axle, the angle between the links exceeds 180° as shown in FIG. 8c. This action tends to lock the canopy in the open position prior to rotation and is made possible because the pin 88 (see FIG. 2) is moved distally beyond the location of pins 84, 86. This can also be seen well in FIG. 10a. At this location, the radiused surface 76d of the camming link is beyond the distal ends of the clevis shoulders 26a, (26b not shown) and is thus no longer prevented from rotating about the clevis axle 42. Although further distal movement of the camming link 76 is prevented, it will be appreciated that further distal movement of the driving link 28 is not yet prevented by the pin 40 passing through the slot 28a. As shown in the Figures which follow, further rotation of the instrument handle will cause rotation of the expanded canopy about the clevis axle.

As shown in FIGS. 9, 9a, 9b, and 9c, further distal movement of the push rod 18 causes the angling link 78 to rotate about the pins 44 and 90. This results in the rotation of the camming link 76 and gimbal 74 about the clevis axle 42 and rotation of the canopy 50 relative to the longitudinal axis of the instrument.

FIGS. 9, 9a, 9b, and 9c illustrate rotation of the canopy approximately 30° relative to the axis of the instrument. FIGS. 10, 10a, 10b, and 10c illustrate rotation of the canopy approximately 60° relative to the axis of the instrument. FIGS. 11, 11a, 11b, and 11c illustrate rotation of the canopy approximately 90° relative to the axis of the instrument. It will be appreciated from FIG. 11b that further movement of the canopy is impeded.

From the foregoing, those skilled in the art will appreciate that reverse rotation of the handle of the apparatus will reverse the above described movements of the canopy.

FIGS. 12 and 12a-12c illustrate the presently preferred embodiment of the handle assembly 24. The handle assembly 24 includes three components: the handle 24a, the knob 24b, and the "nut" 24c which resembles a spool. The handle 24a is coupled to the proximal end 14 of the hollow tube 12 (FIG. 1) by means of a pin 32c which passes through holes 14a in the tube as seen best in FIGS. 12 and 12a. It should be noted that the pin 32c passes through a slot 20a in the proximal end 20 of the push rod 18. The slot and pin engagement allow the push rod to move through the tube and also prevent rotation of the tube. It will be recalled from the description of FIG. 1 that the distal end of the push rod is coupled to the driving link which has a similar pin and slot engagement.

The knob 24b is coupled to the nut 24c by three set screws 34a, 34b, 34c as seen best in FIG. 12c. The nut thus resides inside the handle and rotates with the handle when the handle is rotated. As seen best in FIGS. 12 and 12a, the nut 24c threadably engages the lead screw 22 which is coupled to the proximal end of the push rod. The knob 24b is provided with an annulus 24b' which is engaged by two pins 32a, 32b which pass through the handle 24a. This engagement of the handle and the knob allows the knob to rotate relative to the handle while preventing the knob from moving away from the handle. Those skilled in the art will appreciate that this arrangement of the knob, nut and handle results in longitudinal movement of the push rod when the knob is rotated relative to the handle.

As suggested by the description of FIGS. 12, 12a, 12b, and 12c, the handle assembly is put together in the following order: the handle 24a is coupled to the tube; the nut 24c is coupled to the knob 24b; the nut 24c is coupled to the lead screw; and the knob 24b is coupled to the handle 24a.

There have been described and illustrated herein an endoscopic retractor. While a particular embodiment of the invention have been described, it is not intended that the invention be limited thereto, as it is intended that the invention be as broad in scope as the art will allow and that the specification be read likewise. Thus, while a knob and handle actuator has been disclosed, it will be appreciated that other actuators could be utilized with the canopy end effector assembly. Also, while a canopy has been shown to be made of multiple hinged segments, it is possible to create a canopy from a single sheet of appropriate material such as nitinol. Moreover, while the invention has been show with a rigid tube and push rod, it may be possible to use a flexible tube and push wire if the distal end of the tube is stabilized prior to opening the canopy. Furthermore, while the push rod has been disclosed as having a proximal lead screw and a distal driving link attached to it, it will be understood that these three pieces could be manufactured as a single piece. In addition, while the canopy has been described as being substantially cylindrical when collapsed, it could be arranged to be other shapes such as hexagonal, square, etc. It could also be a cylinder portion. Further, when deployed, the canopy could form a convex, concave, or substantially planar surface.

In addition, although the described embodiment of the invention is well equipped to be delivered to the surgical site through a trocar tube or the like, it should be understood that the canopy portion of the invention could be used with a different type of actuator. For example, the canopy apparatus could be used with an instrument having a shaft with an external push rod extending alongside the shaft. It will therefore be appreciated by those skilled in the art that yet other modifications could be made to the provided invention without deviating from its spirit and scope as so claimed.

The invention claimed is:

1. A surgical instrument, comprising:
a) a shaft having a proximal end and a distal end;
b) a push rod having a proximal end and a distal end and extending substantially parallel to said shaft;
c) actuation means coupled to said proximal end of said shaft and said proximal end of said push rod for moving said push rod relative to said shaft; and
d) a multi-segment canopy coupled to said distal end of said shaft and said distal end of said push rod, wherein movement of said push rod in a first direction causes said multi-segment canopy to move from a substantially cylindrical configuration wherein segments of the canopy are arranged to form a circle to a substantially planar configuration wherein the segments are spread out to form a substantially continuous substantially planar surface, and movement of said push rod in a second direction opposite said first direction causes said multi-segment canopy to move from said substantially continuous substantially planar surface to said substantially cylindrical configuration.

2. A surgical instrument according to claim 1, wherein: said shaft is hollow and said push rod extends through said hollow shaft.

3. A surgical instrument according to claim 1, wherein: said actuation means includes a rotatable knob coupled to said push rod such that rotation of said knob causes translation of said push rod.

4. A surgical instrument according to claim 1, further comprising:
e) an articulate linkage coupling said multi-segment canopy to said push rod, such that movement of said push rod in a first direction causes said multi-segment canopy to move from a substantially cylindrical configuration to a substantially planar configuration and then further movement of said push rod in said first direction causes said multi-segment canopy to angle relative to said shaft.

5. A surgical instrument according to claim 1, wherein: said canopy, when in said substantially cylindrical configuration is dimensioned to fit through a trocar tube.

6. A surgical instrument according to claim 1, wherein: said canopy, when in said substantially cylindrical configuration has a diameter of approximately 15 mm.

7. A surgical instrument according to claim 1, wherein: each of said segments of said multi-segment canopy is substantially arcuate.

8. A surgical instrument according to claim 1, wherein: each of said segments of said multi-segment canopy is hingedly coupled to another of said segments.

9. A surgical instrument according to claim 8, wherein: at least one of said segments is hingedly coupled with a hinge stop to another of said segments.

10. A surgical instrument according to claim 1, wherein: said multi-segment canopy includes two canopy end segments.

11. A surgical instrument according to claim 10, wherein: each of said end segments is rotatably coupled to an arm such that spreading of said arms causes said canopy to move from said substantially cylindrical configuration to said substantially planar configuration.

12. A surgical instrument according to claim 1, wherein: each of said segments of said multi-segment canopy is hingedly coupled to another of said segments by a torsion spring.

13. A surgical instrument according to claim 1, further comprising:
e) a clevis coupled to said distal end of said shaft, said clevis having at least one longitudinal shoulder; and
f) a linkage coupled to said distal end of said push rod and said multi-segment canopy, wherein
movement of said linkage relative to said clevis is limited by said shoulder.

14. A surgical instrument according to claim 13, wherein: said clevis and said linkage are arranged such that said shoulder permits longitudinal movement of said linkage relative to said clevis until said linkage reaches a location upon which it is free to rotate relative to said clevis.

15. A surgical instrument, comprising:
a) a shaft having a proximal end and a distal end;
b) a push rod having a proximal end and a distal end and extending substantially parallel to said shaft;
c) actuation means coupled to said proximal end of said shaft and said proximal end of said push rod for moving said push rod relative to said shaft;
d) an articulate linkage coupled to said distal end of said shaft and said distal end of said push rod; and
e) an end effector coupled to said articulate linkage, such that movement of said push rod in a first direction causes said articulate linkage to move first linearly and rotationally in a first direction and then further movement of said push rod in said first direction causes said articulate linkage to move rotationally in a second direction.

16. A surgical instrument according to claim 15, wherein:
said end effector includes a member which is substantially cylindrical in a first configuration and which assumes a substantially planar configuration when said articulate linkage is moved linearly.

17. A surgical instrument according to claim 16, wherein:
said end effector in said substantially planar configuration is moved angularly relative to said shaft when said articulate linkage is moved rotationally.

18. A surgical instrument according to claim 15, wherein:
said actuation means includes a rotatable knob coupled to said push rod such that rotation of said knob causes translation of said push rod.

19. A surgical instrument according to claim 16, wherein:
said end effector member, when in said substantially cylindrical configuration is dimensioned to fit through a trocar tube.

20. A surgical instrument according to claim 16, wherein:
said end effector member, when in said substantially cylindrical configuration has a diameter of approximately 15 mm.

21. A surgical instrument according to claim 15, wherein:
said end effector member includes two ends, and
each of said two ends is rotatably coupled to an arm such that spreading of said arms causes said end effector member to move from said substantially cylindrical configuration to said substantially planar configuration.

22. A surgical instrument according to claim 15, wherein:
said articulate linkage includes an angling link coupled to a camming link.

23. A surgical instrument according to claim 22, wherein:
said articulate linkage includes a pair of actuation links coupled to said camming link,
said actuation links defining an angle between them and being movable from an angle of less than 90° to an angle of approximately 180°.

24. A surgical instrument according to claim 23, wherein:
said articulate linkage includes a rotatable gimbal coupled to said actuation links, such that
said gimbal is rotated after said arms are moved to define an angle of approximately 180°.

25. A surgical instrument according to claim 24, further comprising:
e) a clevis coupled to the distal end of the shaft and engaged by said articulate linkage, said clevis including anti-rotation means for preventing rotation of said gimbal until said push rod is at a predetermined location.

26. A surgical instrument according to claim 15, wherein:
said shaft is hollow and said push rod extends through said hollow shaft.

27. A surgical instrument, comprising:
a) a shaft having a proximal end and a distal end;
b) a push rod having a proximal end and a distal end and extending substantially parallel to said shaft;
c) actuation means coupled to said proximal end of said shaft and said proximal end of said push rod for moving said push rod relative to said shaft; and
d) an end effector assembly including two substantially parallel arms, wherein
movement of said push rod in a first direction causes said substantially parallel arms to move apart from each other while remaining substantially parallel to define an imaginary plane extending between them, and further movement of said push rod in said first direction causes said arms to move such that said imaginary plane assumes an angle relative to said shaft.

28. A surgical instrument according to claim 27, wherein:
said shaft is hollow and said push rod extends through said hollow shaft.

29. A surgical instrument according to claim 27, wherein said end effector assembly includes a flexible member extending between said two arms.

30. A surgical instrument according to claim 27, wherein:
said flexible member assumes a substantially cylindrical configuration when said arms are closest together and assumes a substantially planar configuration when said arms are farthest apart.

31. A surgical instrument according to claim 30, wherein:
said flexible member is a multi-segment member.

32. A surgical instrument according to claim 31, wherein:
said two arms remain substantially parallel to each other.

33. A surgical instrument, comprising:
a) a shaft having a proximal end and a distal end;
b) a push rod having a proximal end and a distal end and extending substantially parallel to said shaft;
c) actuation means coupled to said proximal end of said shaft and said proximal end of said push rod for moving said push rod relative to said shaft;
d) a pair of substantially parallel arms coupled to said distal ends of said shaft and said push rod such that movement of said push rod relative to said shaft moves said arms relative to each other; and
e) a flexible member coupled to said substantially parallel arms, wherein said substantially parallel arms define an imaginary plane, said flexible member defines a volume between it and said imaginary plane, and movement of said substantially parallel arms changes said volume with said substantially parallel arms remaining substantially parallel to each other.

34. A surgical instrument according to claim 33, wherein:
said shaft is hollow and said push rod extends through said hollow shaft.

35. A surgical instrument according to claim 33, wherein:
said substantially parallel arms remain substantially parallel during substantially all of their movement.

36. A surgical instrument according to claim 33, wherein:
said actuation means includes a rotatable knob coupled to said push rod such that rotation of said knob causes translation of said push rod.

37. A surgical instrument according to claim 33, further comprising:
f) an articulate linkage coupling said substantially parallel arms to said push rod, such that
movement of said push rod in a first direction causes said arms to move apart and then angle relative to said shaft.

38. A surgical instrument according to claim 33, wherein:
said flexible member is a multi-segment canopy.

39. A surgical instrument according to claim 38, wherein:
said multi-segment canopy includes two canopy end segments, and
each of said end segments is coupled to one of said arms.

40. A surgical instrument, comprising:
a) a shaft having a proximal end and a distal end;
b) a push rod having a proximal end and a distal end and extending substantially parallel to said shaft;
c) actuation means coupled to said proximal end of said shaft and said proximal end of said push rod for moving said push rod relative to said shaft; and d) a multi-segment canopy coupled to said distal end of said shaft and said distal end of said push rod, such that movement of said push rod in a first direction causes said multi-segment canopy to move from a first compact configuration to a second expanded configuration and then rotate after being fully expanded, and movement in a second direction opposite said first direction causes said multi-segment canopy to move from said second expanded configuration to said first compact configuration.

41. A surgical instrument according to claim 40, wherein:
said shaft is hollow and said push rod extends through said shaft.

42. A surgical instrument according to claim 40, wherein:
said actuation means includes a rotatable knob coupled to said push rod such that rotation of said knob causes translation of said push rod.

43. A surgical instrument according to claim 40, further comprising:

e) an articulate linkage coupling said multi-segment canopy to said push rod, such that movement of said push rod in a first direction causes said multi-segment canopy to move from said first configuration to said second configuration and then angle relative to said shaft.

44. A surgical instrument according to claim 40, wherein:
said canopy, when in said first configuration is dimensioned to fit through a trocar tube.

45. A surgical instrument according to claim 40, wherein:
said canopy, when in said first configuration is dimensioned to fit through a trocar tube having a diameter of approximately 15 mm.

46. A surgical instrument according to claim 40, wherein:
each of said segments of said multi-segment canopy is substantially arcuate.

47. A surgical instrument according to claim 40, wherein:
each of said segments of said multi-segment canopy is hingedly coupled to another of said segments.

48. A surgical instrument according to claim 47, wherein:
at least one of said segments is hingedly coupled with a hinge stop to another of said segments.

49. A surgical instrument according to claim 47, wherein:
at least one of said segments is coupled to another of said segments with a torsion spring.

50. A surgical instrument according to claim 40, wherein:
said multi-segment canopy includes two canopy end segments.

51. A surgical instrument according to claim 50, wherein:
each of said end segments is coupled to a rotatable arm such that spreading of said rotatable arms causes said canopy to move from said first configuration to said second configuration.

52. A surgical instrument, comprising:

a) a shaft having a proximal end and a distal end;

b) a push rod having a longitudinal axis, a proximal end and a distal end and extending substantially parallel to said shaft;

c) actuation means coupled to said proximal end of said shaft and said proximal end of said push rod for moving said push rod relative to said shaft; and d) a multi-segment canopy having a plurality of segments hingedly coupled to each other with hinge axles substantially parallel to said longitudinal axis, said canopy being coupled to said distal end of said shaft and said distal end of said push rod, wherein movement of said push rod in a first direction causes said multi-segment canopy to move from a substantially cylindrical configuration wherein segments of the canopy are arranged in a circle to a substantially planar configuration wherein the segments are spread out to form a substantially continuous substantially planar surface.

\* \* \* \* \*